United States Patent [19]
Burd

[11] 4,133,312
[45] Jan. 9, 1979

[54] CONNECTOR FOR ATTACHMENT OF BLOOD TUBING TO EXTERNAL ARTERIOVENOUS SHUNTS AND FISTULAS

[75] Inventor: Samuel Burd, Oakland, Calif.
[73] Assignee: Cordis Dow Corp., Miami, Fla.
[21] Appl. No.: 731,865
[22] Filed: Oct. 13, 1976
[51] Int. Cl.² ............... A61M 5/00; F16L 47/00
[52] U.S. Cl. ..................... 128/214 R; 128/247; 128/348; 285/12; 285/332; 285/423
[58] Field of Search ............. 128/214 R, 214.2, 221, 128/218 N, 247, 348, 334 C, 215; 285/174, 242, 423, 12

[56] References Cited
U.S. PATENT DOCUMENTS

| | | | |
|---|---|---|---|
| 1,173,718 | 2/1916 | Hirst | 285/12 |
| 1,793,068 | 2/1931 | Dickinson | 128/221 |
| 2,076,121 | 4/1967 | Dickinson | 128/221 |
| 2,870,765 | 1/1959 | Henderson | 128/215 |
| 2,880,722 | 4/1959 | Dickinson | 285/242 |
| 3,344,786 | 10/1967 | Berg et al. | 128/215 |
| 3,394,954 | 7/1968 | Sarns | 285/423 X |
| 3,876,234 | 4/1975 | Harms | 285/423 X |
| 3,882,862 | 5/1975 | Berend | 128/348 X |
| 3,967,836 | 7/1976 | Izzi | 285/12 |
| 3,977,403 | 2/1975 | Patel | 128/247 X |

Primary Examiner—Dalton L. Truluck
Attorney, Agent, or Firm—Neal A. Waldrop

[57] ABSTRACT

A universal connector for a blood tubing set having a blood tube attached to one end portion and alternative means on the other end portion of said connector for selectively connecting and locking to the blood tube an external arteriovenous shunt, or a fistula.

5 Claims, 7 Drawing Figures

U.S. Patent  Jan. 9, 1979  Sheet 1 of 2  4,133,312
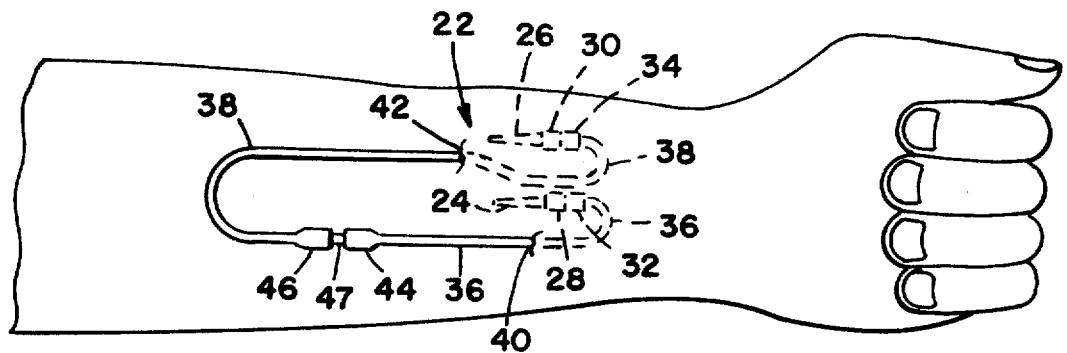
FIG _ 1
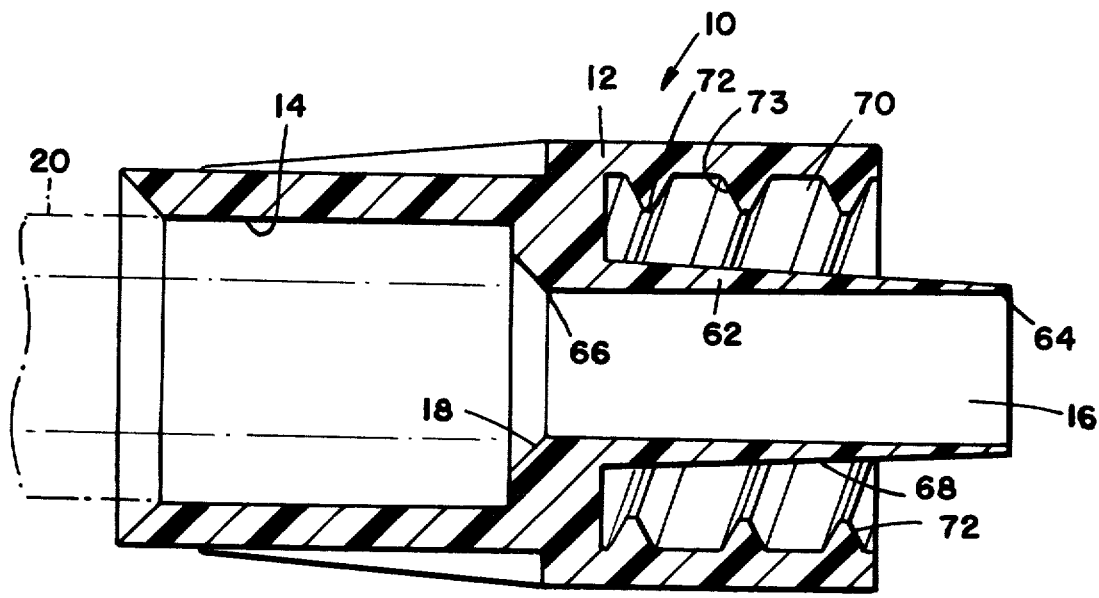
FIG _ 2
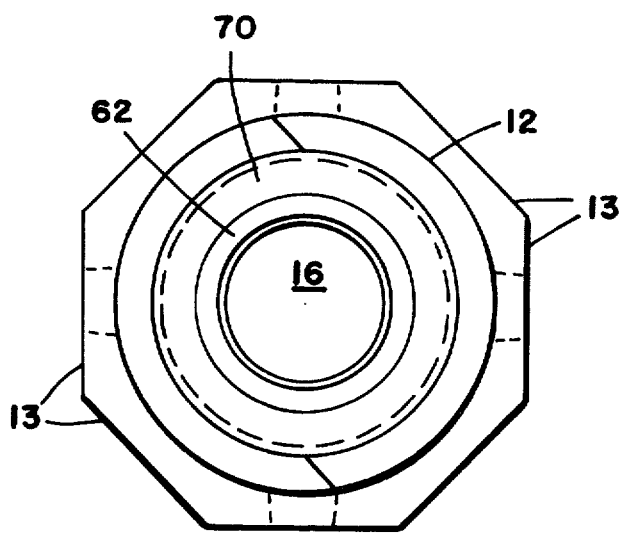
FIG _ 3

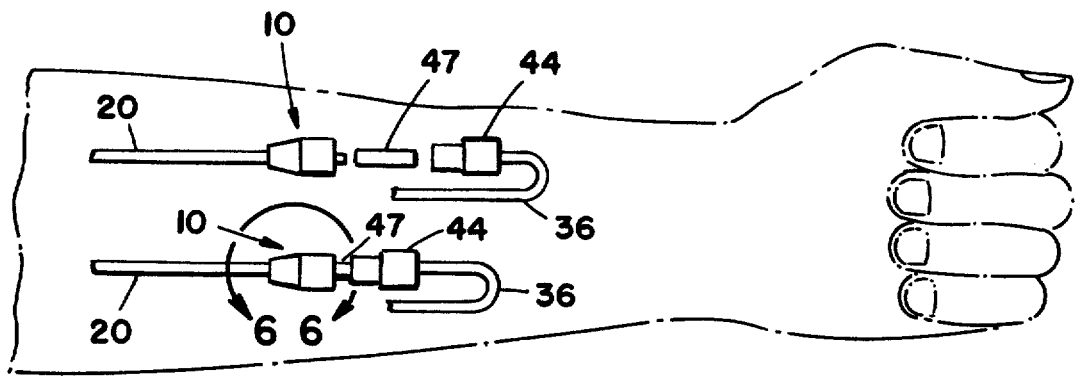
FIG _ 4
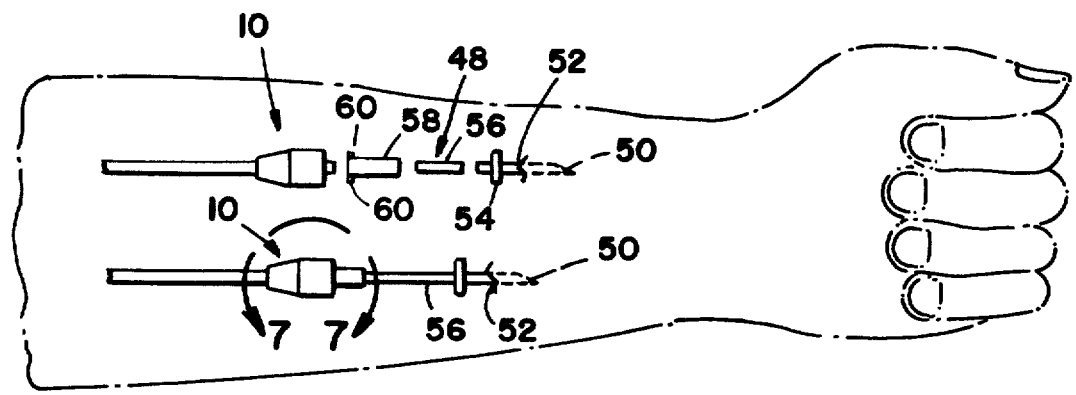
FIG _ 5
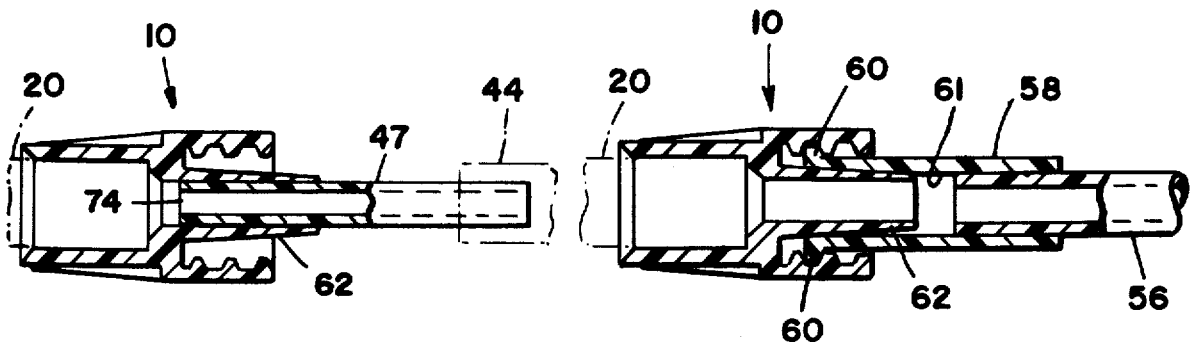
FIG _ 6     FIG _ 7

CONNECTOR FOR ATTACHMENT OF BLOOD TUBING TO EXTERNAL ARTERIOVENOUS SHUNTS AND FISTULAS

BACKGROUND OF THE INVENTION

Access to the bloodstream of a patient receiving intermittent dialysis for a chronic renal failure is necessary throughout the dialysis which may require from two to six hours. Earliest access employed cannulas, that is, hollow glass or metal tubes inserted into an artery and a vein. Repeat need for access brought about a substitution of plastic for the glass or metal cannula and during the 1950's, the external ends of the plastic cannulas were connected with a short length of plastic tubing thereby short circuiting the arterial blood into the vein; this provided an external, available access to the blood stream for repeated dialyses without the necessity for needle penetration of the artery and vein for each dialysis. Such external arteriovenous shunts are currently in use on a portion of those patients receiving intermittent hemodialysis with artificial kidneys. Connection to the artificial kidney is made by attaching blood tubing from the artificial kidney to the external connectors on each of the two portions of the external plastic tubes forming the arteriovenous shunt.

By 1960, problems with the blood flowing in the external plastic tubes of the shunt during the time between dialyses, such as clotting, infection and inadvertent separation of the external tube connector, led to an alternative shunt system. In this system, an artery is shunted to a vein entirely under the skin and the shunt is left in place indefinitely. Resultant enlarged veins provide access sites for penetration with a fistula. Fistulas, each consisting of a needle attached to a short section of blood tubing terminating at its outer end in a connector, are then attached to blood tubes associated with the artificial kidney. Access to the bloodstream by fistula is currently used to a greater extent in artificial kidney dialysis than external arteriovenous shunts.

One problem is ever present in delivering blood from the patient to an artificial kidney irrespective of whether the blood access is by fistula or from an external arteriovenous shunt. That problem is inadvertent separation of the members linking the blood tubes to the blood access source. Typically, the connector consists of a short length of Teflon tubing, having its outer surface etched and its ends smooth and slightly beveled for snug fit into a tapered bore of the connector body on the fistula or external shunt, and a similar bore available on the blood tube. After the connection is made by firmly pressing the connector parts together, and overlying tape is applied, the joint is nevertheless subject to forceful disconnection at any time during the two to six-hour period the dialysis is in progress. Although accidental disconnection occurs only during a small fraction of the time, it is traumatic when it does occur and can cause death unless immediate corrective steps are taken to stop the loss of blood.

The improved connector of this invention provides a locking connection that prevents accidental disengagement of the blood tube from the blood access fistula or external shunt and concurrently provides an available alternative tapered connector of the type heretofore used. No connector providing such alternative connections has been available heretofore to the best of applicant's knowledge.

BRIEF SUMMARY OF THE INVENTION

This invention provides a universal connector for joining a blood tube to a blood access fistula or an external arteriovenous shunt by either a conventional tapered surface press fit or a locking connection.

The connector of this invention is simple, easy to manufacture and provides an improved tapered sleeve for pressure fit connections relative to the heretofore available Luer slip connections which use the standard Luer taper for medical applications for glass and metal, Z 70.1-1955, approved Aug. 16, 1955. This tapered sleeve is more gradually tapered than the Luer slip connector on its inner wall surface to form a leak-tight pressure fit with present day conventional Teflon tube connectors; it is preferably more tapered on its outer wall surface that is received by the mating inner surface of a connector located at the exit end of a fistula or external arteriovenous shunt. This exit end of the fistula or shunt connector is also provided with male projections on its outer surface which interfit into internal threads carried by the universal connector end of the connector of this invention to thereby lock together the blood tube and such blood access connector.

The alternative connecting members on the universal connector end of the connector of this invention make it suitable for use with all types of connectors on external arteriovenous shunts and fistulas in current use in the United States; it provides in a single member the first known connector providing conventional connector means and a combination seal-lock means which locks to prevent accidental disconnection during dialysis with artificial kidney.

DESCRIPTION OF THE DRAWINGS AND DETAILED DESCRIPTION OF THE INVENTION

FIG. 1 is a view illustrating a typical external arteriovenous shunt in place in and on the arm of a patient;

FIG. 2 is a cross-sectional view of the universal connector of this invention;

FIG. 3 is an end view of the connector of FIG. 2;

FIG. 4 is a view showing in approximate location on an arm, in phantom, an exploded and connected form of a connection between a blood tube carrying the universal connector of this invention and an end of an external arteriovenous shunt;

FIG. 5 is a view showing in approximate location on an arm, in phantom, an exploded and connected form of a connection between a blood tube carrying the universal connector of this invention and an end of a fistula having male locking projections thereon;

FIG. 6 is a view partly in section showing the connection between the parts within the circular area 6—6 of FIG. 4; and FIG. 7 is a view partly in section showing the connection between the parts within the circular area 7—7 of FIG. 5.

Referring to the drawings, the universal connector of this invention is most completely shown in FIG. 2 and is generally designated 10. Connector 10 consists of a body 12 having a bore therethrough, which bore consists of a large diameter portion 14 and a smaller diameter portion 16 communicating therewith and connected thereto by bevel portion 18. Large diameter bore 14 has a size selected so as to snugly receive the outer wall surface of the end of a conventional blood tube 20, which is normally secured therein by solvent softening of the mating surfaces and then pressing the parts together.

The body 12 is preferably fabricated from a plastic which is susceptible to softening by the same solvent which softens the material used in the blood tube 20, typically, a plasticized polyvinyl chloride; body 12 may be fabricated from any of a wide variety of semi-rigid to rigid plastic materials or metals which resist corrosion from blood, saline solutions and other physiologic solutions or medicants ordinarily encountered in the use of blood tubing; for example, semi-rigid polyvinyl-chloride polymers, semi-rigid silicone resins or polyurethanes or polycarbonates. A preferred material is a co-polymer of propylene-vinyl chloride available commercially under the designation StaFlow from Air Products and Chemicals of Wayne, Pa. Stainless steel and other corrosion resistant nickel-chromium alloys are suitable.

In the event the material selected for body 12 is not plastic, or is not a plastic softenable by the solvent which also softens the blood tube, attachment of the bloodtube to one end of body 12 may be made by using an adhesive between the outer surface of blood tube 20 and the inner surface of bore 14, or with various types of mechanical connectors well known to those skilled in this art.

The universal-connector end of body 12, that is the end opposite from the end into which the blood tube 20 is attached, contains the combination of interrelated and interfunctional means so located and arranged as to provide the improved alternative connector construction that distinguishes this invention from heretofore known connectors in use in connection with blood tube sets.

A typical arteriovenous shunt is shown in FIG. 1 in a preferred location on a patient's inner arm spaced from the wrist and is generally designated 22. Shunt 22 consists of a typical Teflon tip 24 which is positioned beneath the skin in communication with an artery or vein, and a second Teflon tip 26 which completes the blood circuit from tip 24 to either an artery or vein, as required. Tips 24, 26 have connectors 28, 30 respectively, which connect with associated silicone rubber connectors 32, 34 respectively, which in turn, interconnect with silicone rubber tubing 36, 38 respectively. Tubing 36, 38 extends through the patient's skin at 40, 42 respectively, and are externally connected by silicone rubber body connector members 44, 46 each of which snugly receives a press-fit Teflon tube connector 47, the outer surface of which is roughened, as by etching.

A typical fistula is illustrated in FIG. 5 and is generally designated 48. Fistula 48 consists of a needle 50 which pierces the skin at 52 and communicates with an artery or vein at its inner end in a conventional manner. The outer end of needle 50 is provided with projecting wing members 54 which enable secure attachment of the needle to the skin to prevent unintentional withdrawal during dialysis and is connected to a short length of blood tubing 56, terminating at its outer end in a connector 58 bearing on its peripheral surface, near the outer extremity, a plurality of male tabs or projections 60, and a tapered inner bore 61, as may be seen in FIG. 7. Projections 60 are circumferentially spaced apart, in opposing pairs, and preferably are 4 to 6 in number, although two projections may be used satisfactorily. Projections 60 may be axially spaced inwardly from the outer end extremity of connector 58 a small distance or immediately adjacent to the outer end surface, as desired. The interrelationship between the thread on the universal-connector end of connector 10 and the projections 60 to effect a locking relationship and simultaneously effect the leak-tight fit between fistula 48 and connector 10 will be explained in greater detail below, particularly in connection with FIG. 7. Projections 60 should be fabricated with sufficient width, in the axial direction, to withstand the substantial pressure that may be needed to effect a tight leak-free connection, and preferably are tapered, from thin to broad, in the circumferential direction of rotation to lock.

Returning, now to the novel construction of the universal-connector end of connector 10, body 12 is multifaceted, e.g., octagonal as indicated at 13, and is provided with outwardly projecting sleeve 62 which defines small diameter opening 16. The inner surface of sleeve 62 is very gradually tapered from the diameter 64 at its extreme outer end to its inner end 66, for example, at less than about 0.02"/inch. The outer surface 68 of sleeve 62 is also tapered from its smallest diameter, at its outer end, to its largest diameter, at its inner end, and the taper preferably is greater than the conventional taper on a Luer slip connection, for example, about 0.07 inch taper per inch to about 0.1 inch taper per inch.

Octagonal end portion 13 is provided wtih a plurality of internal threads having an outer diameter 70 and an inner diameter 72 with sloping interconnecting wall portions 73 against which projections 60 bear as a locking connection is established between fistula 48 and connector 10.

As may be seen in FIG. 2 and 7, internal communication between fistula blood tube 56 and sleeve 62 of universal connector 10 is established as projection 60 moves inwardly by rotation against thread wall 73; the length of taper surface contact between the inner surface 61 of connector 58 and the outer tapered wall 68 of sleeve 62 is determined partially by the location of projection 60 closely adjacent the outer end of connector 58, as shown, or spaced from that end surface. With projection 60 adjacent the end surface of connector 58 and tightened into the innermass thread position space still remains between the outer end of sleeve 62 and the inner end of blood tube 56; by moving projection 60 axially away from the end surface of connector 58 and then tightening that projection to the innermost possible location, more sealing pressure is exerted on the mating tapered surfaces 61 and 68 and the length of contact is also extended until, at the maximum, there is contact between the outer end of sleeve 62 and the inner end of blood tube 56. This location for projections 60 is preferred for uses in which the pressure contemplated during use is expected to exceed the approximately −80 mm Hg that is experienced in normal dialysis using a hollow fiber artificial kidney such as the C-DAK artificial kidney available from Cordis Dow Corp.

In the alternative non-locking connection use of connector 10, the relationship of parts is best seen in FIG. 6. Teflon connector 47, having an etched outer surface, is pressed into fluid-tight sealing relationship against the gradually tapered inner wall 64, 66 of sleeve 62 of connector 10, preferably into close adjacency with the inner end of blood tube 20, as indicated at 74.

It is to be understood that the positioning of projections 60 on fistula connector 58 is illustrative only and that this invention contemplates that Teflon connector 47 shown in FIG. 1, 4 and 6 may be replaced by connector 58, or its equivalent, when it is desired to attain the positive locking characteristics described above in connection with FIGS. 2, 5 and 7 for external arteriovenous shunts.

What I claim is:

1. A universal connector having a blood tube connector on one end and universal connector means on the opposite end comprising a first means and a second means for selective connection and disconnection on the inner or outer tapered surface of a common sleeve member with the connector portion of a fistula and of an external arteriovenous shunt, said first means comprising a gradually inwardly end to end tapering internal surface for a press fit connection between mating surfaces on said connector portion and said internal surface, and said second means comprising an outwardly end to end tapering external surface of said first means and a threaded portion encircling a portion of the length of said first means for forming a locking connection between the connector portion of a fistula and an external arteriovenous shunt between mating surfaces on said connector portion and said externally tapered surface on said first means and said threaded portion thereby effecting a selected fluid-tight seal between said connector portion of said fistula and said external arteriovenous shunt and said first and said second means of said universal connector means.

2. A universal connector in accordance with claim 1 wherein said universal connector comprises a body having a blood passageway therethrough and wherein said first means comprises a sleeve member defining a portion of said passageway, the outer end of which projects from said body, said sleeve member being defined by a wall, said wall having an inner surface which tapers gradually from its largest diameter at its outer end to its smallest diameter at its inner end, and an outer surface which tapers from its smallest diameter at its outer end to its largest diameter at its inner end at a taper substantially greater than the taper on said inner surface, said press fit connection being effected by contact between said tapered inner surface of said sleeve wall and the outer mating surface of the connector of a blood access device selected from the group consisting of a fistula and an external arteriovenous shunt.

3. A universal connector in accordance with claim 1 wherein said universal connector comprises a body having a blood passageway therethrough and wherein said second means comprises a sleeve member defining a portion of said passageway, the outer end of sleeve member projecting outwardly beyond said universal connector end of said body and the inner end terminating in adjacency to the inner end of said blood tube connector, said sleeve member having an outer wall portion which tapers from its smallest diameter at its outer end to its largest diameter at its inner end, and a plurality of threads in said body surrounding a portion of the length of said sleeve, the inner diameter of said threads being larger than the diameter of the said tapered outer wall of said sleeve at its inner end, said fluid-tight seal being effected by contact between said tapered outer surface of said sleeve and the inner mating surface of the connector of a blood access device selected from the group consisting of a fistula and an external arteriovenous shunt and said locking connection being effected by pressure contact between said threads and projections extending outwardly from the peripheral surface adjacent the inner end of said connector of said blood access device which effects said fluid-tight seal.

4. A blood tube set comprising a length of blood tubing having attached to at least one end thereof a universal connector comprising a sleeve defined by a wall portion, said wall portion being tapered on its inner surface gradually from end to end from a larger diameter at its outer end to a smaller diameter at its inner end, said wall portion being tapered on its outer surface from end to end inwardly from a smaller to a larger diameter at a degree of taper in excess of the degree of taper on said inner surface, said sleeve selectively forming a press fit connection with said inner tapered surface and a locking connection with said outer tapered surface and the mating surface of the connector portion of a blood access device selected from the group consisting of a fistula and an external arteriovenous shunt.

5. A blood tube set as claimed in claim 4 wherein said universal connector is the connector defined in claim 1.

* * * * *